United States Patent [19]

Buchwald et al.

[11] Patent Number: 6,166,226
[45] Date of Patent: *Dec. 26, 2000

[54] SYNTHESIS OF ARYL ETHERS

[75] Inventors: Stephen L. Buchwald, Newton; John P. Wolfe, Brighton; Michael Palucki, Somerville, all of Mass.

[73] Assignee: Massachusetts Institute of Technology, Cambridge, Mass.

[*] Notice: This patent is subject to a terminal disclaimer.

[21] Appl. No.: 09/206,820

[22] Filed: Dec. 8, 1998

Related U.S. Application Data

[63] Continuation of application No. 08/728,449, Oct. 10, 1996, Pat. No. 5,847,166.

[51] Int. Cl.[7] .................... C07D 313/00; C07D 319/06; C07D 311/92; C07D 255/00; C07D 43/20

[52] U.S. Cl. .................... 549/355; 549/388; 549/398; 549/469; 558/423; 568/630; 568/631; 568/657

[58] Field of Search .................... 549/355, 388, 549/398, 469; 558/423; 568/630, 631, 657

[56] References Cited

U.S. PATENT DOCUMENTS 5,847,166  12/1998  Buchwald ........................ 549/355

OTHER PUBLICATIONS

Guram et al. "A simple Catalytic Method for the Conversion of Aryl Bromides to Arylamines" Angew. Chem. Int. Ed. Engl. 34 (12):1348 (Jul., 1995).

Wolfe et al. "An Improved Catalyst System for Aromatic Carabon–Nitrogen Bond Formation: The Possible Involvement of Bis(Phosphine) Palladium Complexes as Key Intermediates" J. Am. Chem. Soc. 118:7215 (Jul., 1996).

M.S. Driver and J.F. Hartwig "A Second Generation Catalyst for Aryl Halide Amination: Mixed Secondary Amines from Aryl Halides and Primary Amines Catalyzed by (DPPF)PdCl$_2$" J. Amer. Chem. Soc. 118:7217 (Jul., 1996).

A.J. Buchwald and S.L. Buchwald "Novel Synthesis of Tetrahydropyrroloquinolines: Applications to Alkaloid Synthesis" J. Amer. Chem. Soc. 118:1028 (Feb., 1996).

J.P. Wolfe and Stephen L. Buchwald "Palladium–Catalyzed Amination of Aryl Iodides" J. Organic Chem. 61(3): 1133 (Feb., 1996).

H–J Cristau and J–R Desmurs "Arylation of Hard Heteroaromatic Nucleophiles Using Bromoarenes Substrates and Cu, Ni, Pd Catalysts" Ind. Chem. Libr. 7:240 (Jan., 1995).

Cacchi et al. "Palladium–Catalyzed Carbonylation of Aryl Triflates. Synthesis of Arenecarboxylic Acid Derivatives from Phenols" Tetrahedron Lett. 27(3):3931 (1986).

Komiya et al. "Reductive Elimination of Aryl Carboxylates from Acyl(aryloxy)nickel(II) and–palladium (II) Complexes" Organomet. 4:1130 (1985).

J. Louie and J.F. Hartwig "Palladiu–Catalyzed Synthesis of Arylamines from Aryl Halides. Mechanistic Studies Lead to Coupling in the Absence of Tin Reagents" Tetrahedron Lett. 36(21): 3609 (May, 1995).

Houghton et al. "Reactions of Co–ordinated Ligands. Part 10. Rhodium–catalyzed Cyclisation of 3–(2–Fluorophenyl-)propanols to Chromans" J. Chem. Soc. Perkins Trans. 1984:925 (1984).

R.P. Houghton and M. Voyle "Intramolecular Nucleophilic Substitution of Co–ordinated Aryl Halides. A Preparation of Chromans" J.C.S. Chem. Comm. 1980:884 (1980).

R. Cramer and D.R. Coulson Nickel–Catalyzed Displacement Reactions of Aryl Halides J. Org. Chem. 40(16):2267 (Aug., 1975).

Larock et al. "Heteroannulation via Intramolecular ($\pi$–Allyl)palladium Displacement" J. Org. Chem. 49:3662 (1984).

Stanton et al. "Alkoxides as Nucleophiles in ($\pi$–Allyl)palladium Chemistry. Synthetic and Mechanistic Studies" J. Am. Chem. Soc. 105:1964 (1983).

Keegstra et al. "Copper(I) Halide Catalyzed Synthesis of Alkyl Aryl and Alkyl Heteroaryl Ethers" Tetrahedron 48 (17):3633 (1992).

Kindu et al. "Palladium–catalysed Heteroannulation of Acetylenic Compound: a Facile Method for the Synthesis of Benzofurans" J. Chem. Soc., Chem. Comm. 1992:41.

Bates, R. B., et al., "High–Yield Benzyne Synthesis of Diaryl Ethers", *J. Org. Chem.*, vol. 47, pp. 4374–4376 (1982).

Migita, T., et al., "The Palladium Catalyzed Nucleophilic Substitution of Aryl Halides by Thiolate Anions", *The Chemical Society of Japan*, vol. 53, pp. 1385–1389 (1980).

Palucki, M., et al., "Synthesis of Oxygen Heterocycles via a Palladium–Catalyzed C–) Bond–Forming Reaction", *J. Am. Chem. Soc.*, vol. 118, pp. 10333–10334 (1996).

Palucki, M., et al., "Palladium–Catalyzed Intermolecular Carbon–Oxygen Bond Formation: A New Synthesis of Aryl Ethers", *J. Am. Chem. Soc.*, vol. 118, pp. 3395–3396 (1997).

Zask, A., et al., "Palladium Hydrides in Organic Synthesis. Reduction of Aryl Halides by Sodium Methoxide Catalyzed by Tetrakis (triphenylphosphine) palladium", *J. Org. Chem.*, vol. 43, No. 8 (1978).

*Primary Examiner*—D. Margaret Seaman
*Attorney, Agent, or Firm*—Matthew P. Vincent; Dana M. Gordon; Foley, Hoag & Eliot LLP

[57] ABSTRACT

A method for preparing an aryl ether compound is provided in which an alcohol is reacted with an aromatic compound in the presence of a base, and a transition metal catalyst selected from the group consisting of platinum and nickel to form an aryl ether. The aromatic compound comprises an activated substituent, X, said activated substituent being a moiety such that its conjugate acid HX has a pKa of less than 5.0. The catalyst is preferably a soluble palladium complex in the presence of supporting ligands.

24 Claims, 1 Drawing Sheet

SYNTHESIS OF ARYL ETHERS

RELATED APPLICATIONS

This application is a continuation of U.S. patent application Ser. No. 08/728,449, filed Oct. 10, 1996, which issued as U.S. Pat. No. 5,847,166 on Dec. 8, 1998.

GOVERNMENT SUPPORT

This invention was made with government support under Grant Number 9412982-CHE awarded by the National Science Foundation. The government has certain rights in the invention.

BACKGROUND OF THE INVENTION

The present invention relates to improved methods for preparing aryl ethers which are useful intermediates and end products in pharmaceutical and agricultural applications.

It has been recently reported that aryl bromides react with simple primary and secondary amines in the presence of a palladium catalyst, supporting ligands and Na(OtBu) (base) to form the corresponding arylamine in good yields. See, Guram et al. *Angew. Chem.* 34(12):1348 (1995).

Despite the recent successes with palladium-catalyzed cross-coupling reactions of Ar—X (X=Br) with amines, comparable coupling of aryl halides with alcohols remains elusive, and this in spite of its obvious utility in organic synthesis. Aryl ethers, including oxygen heterocycles, are prominent in a large number of pharmacologically important molecules and are found in numerous secondary metabolites.

Existing methods for the conversion of Ar—X to aryl ethers often require harsh or restrictive reaction conditions and/or the presence of activating groups on the arene ring. For example, the Cu(I)-catalyzed syntheses of aryl and vinyl ethers commonly require large amounts of freshly prepared sodium alkoxides and/or large excess of the corresponding alcohol in order to achieve reasonable yields from the corresponding aryl halides and vinyl halides. See, Keegstra et al. *Tetrahedron* 48(17):3633 (1992).

Cramer and Coulson also reported limited success with the Ni(II)-catalyzed synthesis of diphenyl ether using sodium phenolate at reaction temperatures greater than 200° C. See, *J. Org. Chem.* 40(16):2267 (1975). Christau and Desmurs describe the nickel-catalyzed reactions of alcohols with aryl bromides in the presence of a base. Good yields (ca. 80%) were reported only for reactions with primary alcohols with 7 mol % nickel catalyst at 125° C. *Ind. Chem Libr.* 7:240 (1995). Christau and Desmurs also reported that synthesis of aryl ethers was possible only for primary and secondary alcohols. Houghton and Voyle reported the Rh(III)-catalyzed cyclization of 3-(2-fluorophenyl) propanols to chromans activated by π-bonding to the metal center; however, the reaction required very high rhodium catalyst loading (17 mol %). See, *J. Chem. Soc. Perkin Trans. I*, 925 (1984).

Ether formation has been reported as a minor side product in the palladium-catalyzed carbonylation reactions of highly activated aromatic compound such as α-substituted quinolines. Because of the highly reactive nature of the α-site, it is possible that the reaction proceeds by direct nucleophilic substitution, without promotion or catalysis by the palladium metal center. See, Cacchi et al. *Tet. Lett.* 27(33):3931 (1986).

Thus there remains a need for an effective method of preparing a wide range of aryl ethers under mild conditions and in high yields. There is a further need for an efficient catalytic system with high efficiencies and turnover number for the synthesis of aryl ethers. In addition, there still remains a need for an effective method for the arylation of tertiary alkoxides.

SUMMARY OF THE INVENTION

The present invention provides general and attractive routes to a wide range of aryl ethers. The methods provide several improvements over methods known heretofore, namely, the efficient synthesis of aryl ethers under mild conditions and in high yields. In particular, the method of the invention may be used in coupling reactions using tertiary alcohols. In other aspects of the invention, the invention provides a class of transition metal complexes useful in the catalytic reactions of the invention which were heretofore not known to be useful in the preparation of aryl ethers.

In one aspect of the invention, an aryl ether compound is prepared by reacting an alcohol or its corresponding alkoxide salt with an aromatic compound in the presence of a base and a catalyst selected from the group consisting of complexes of platinum, palladium and nickel. The aromatic compound comprises an activated substituent, X, and the activated substituent is a moiety such that its conjugate acid HX has a pKa of less than 5.0. When the reaction takes place using an alkoxide salt, a base may not be required.

In preferred embodiments, the reaction employs about 0.0001 to 20 mol % catalyst metal, preferably 0.05 to 5 mol % catalyst metal, and most preferably 1 to 3 mol % catalyst with respect to at least one of the alcohol and the aromatic compound. In other preferred embodiments, the reaction is carried out at a temperature in the range of about 50° C. to about 120° C., and preferably in the range of about 65° to about 100° C. In other preferred embodiments, the aryl ether is obtained in greater than 45% yield and preferably in greater than 75% yield. The reaction is substantially complete in less than about 12 hours, preferably in less than about 6 hours and most preferably in less than about 2 hours.

In preferred embodiments, the transition metal catalyst comprises a palladium complex and is preferably a catalyst complex selected from the group consisting of tris (dibenzylideneacetone) dipalladium, palladium acetate and bis(dibenzylideneacetone) palladium. The catalyst complex may comprise a supporting ligand. In preferred embodiments, the supporting ligand is selected from the group consisting of alkyl and aryl derivatives of phosphines, bisphosphines, imines, amines, phenols, arsines, and hybrids thereof. In other preferred embodiments, the supporting ligand is selected from the group consisting of (±)-2,2'-bis (diphenylphosphino)-1,1'-binaphthyl and separate enantiomers thereof; (±)-2,2'-bis(di-p-tolylphosphino)-1, 1'-binaphthyl and separate enantiomers thereof; 1-1'-bis (diphenylphosphino)ferrocene; 1,3-bis(diphenylphosphino) propane; and 1,2-bis(diphenylphosphino)ethane.

In other embodiments, the alcohol and the aromatic compound are present in substantially stoichiometric amounts. In yet other embodiments, either the alcohol or the aromatic compound is present in no greater than a two-fold excess relative to the limiting reagent and preferably in no greater than about a 20% excess relative to the limiting reagent. In other preferred embodiments, no more than 4 equivalents and preferably no more than 2 equivalents of base is present.

By "supporting ligand", as that term is used herein, it is meant a compound added to the reaction solution in an uncomplexed state, but which is capable of binding with the catalyst metal center. Although such interaction is possible, it is not required in order to observe the desirable reaction products, yields and conditions according to the present invention. Alternatively, the supporting ligand may be complexed to the metal center to provide a pre-made catalyst complex comprising the metal and supporting ligand. The invention makes reference to several supporting ligands in an abbreviated form, where BINAP=(±)-2 ,2'-bis (diphenylphosphino)- 1,1'-binaphthyl (or separated enantiomers); Tol-BINAP=(±)-2,2'-bis-(di-p-tolylphosphino)-1, 1'-binaphthyl (or separated enantiomers); dppf=1-1'-bis(diphenylphosphino)ferrocene; ppfa=(±)-N,N-dimethyl-1-[2-(diphenylphosphino)ferrocenyl]ethylamine (or separated enantiomers); ppfe=(±)-(R)-1-[(S)-2-(diphenylphosphino)-ferrocenyl]ethyl methyl ether (or separated enantiomers); dppp=1,3-bis(diphenylphosphino) propane; dppb=1,2-bis(diphenylphosphino)benzene, and dppe=1,2-bis(diphenylphosphino)ethane.

By "functionalized" alcohol or aromatic, as that term is used herein, it is meant a compound containing both the alcohol (or aromatic) moiety and additional functional groups which impart additional functionality or reactivity to the moiety, but which are not altered during the synthetic sequence of the invention.

BRIEF DESCRIPTION OF THE DRAWING

The FIGURE is a scheme illustrating possible reaction steps in the synthesis of aryl ethers according to the method of the invention.

DESCRIPTION OF THE PREFERRED EMBODIMENT

Figure 1:
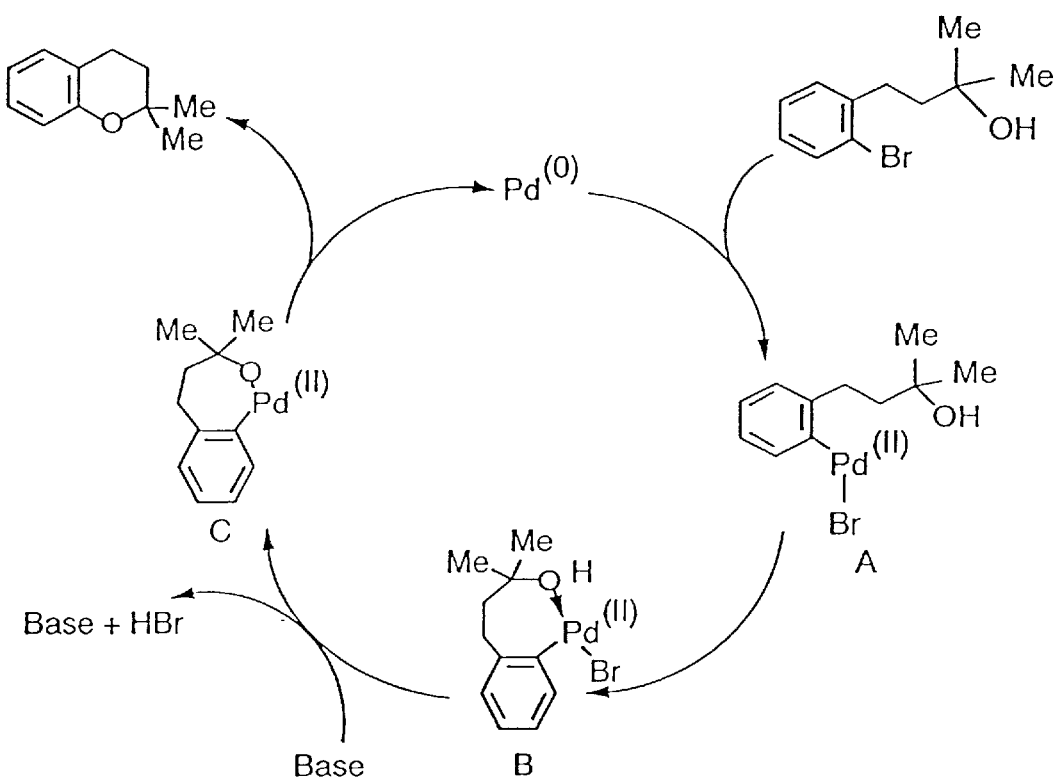

A wide range of alcohols (and alkoxide salts) have been shown to react with aromatic compounds containing an activated substituent (a "good" leaving group) to obtain the corresponding aryl ether. The general reaction is set forth in eq. 1 and is carried out in the presence of a base and a transition metal catalyst complex.

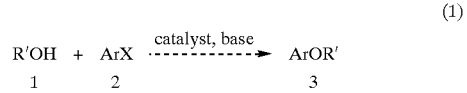

(1)

According to eq. 1, an alcohol 1 is reacted with an aromatic compound 2 having an activated substituent, X, to form an aryl ether 3 in the presence of a catalytic amount of a transition metal catalyst complex and a base. The reaction proceeds at mild temperatures in the presence of a transition metal complex (with or without a supporting ligand) and suitable base. The reaction may be either an intermolecular or intramolecular reaction.

The reaction most likely proceeds via oxidative-addition of the aromatic compound 2 to a zero-valent catalyst metal center, substitution of X by the alcohol 1 at the metal center, followed by reductive-elimination to generate the aryl ether 3. The base presumably promotes formation of an oxygen-metal bond, in which the metal is the metal center of the catalyst, presumably by facilitating proton abstraction from the alcohol hydrogen.

The aromatic compound 2 may be any aromatic compound having a good leaving group. By way of example, the aromatic compound may be selected from the group consisting of phenyl and phenyl derivatives, heteroaromatic compounds, polycyclic aromatic and heteroaromatic compounds, and functionalized derivatives thereof. Suitable aromatic compounds derived from simple aromatic rings and heteroaromatic rings, include but are not limited to, pyridine, imidizole, quinoline, furan, pyrrole, thiophene, and the like. Suitable aromatic compounds derived from fused ring systems, include but are not limited to naphthalene, anthracene, tetralin, indole and the like.

The aromatic compound may have the formula $(Z)_n ArX$, where X is an activated substituent. An activated substituent, X, is characterized as being a good leaving group which readily lends itself to substitution. For the purposes of the present invention, an activated substituent is that moiety whose conjugate acid, HX, has a pKa of less than 5.0. Suitable activated substituents include, by way of example only, halides such as chloride, bromide and iodide, triflate, mesylate, tosylate and diazonium. An additional leaving group may be SR, where R=aryl or alkyl.

Z is an optional substituent on the aromatic ring. Z may be a functional group which imparts additional functionality or reactivity to the aromatic substrate, but which is not altered during the synthetic sequence of the invention. By way of example only, suitable Z include alkyl, aryl, acyl, heteroaryl, amino, carboxylic ester, carboxylic acid, hydrogen group, ether, thioether, amide, carboxamide, nitro, phosphonic acid, hydroxyl, sulfonic acid, halide, pseudohalide groups, and substituted derivatives thereof, and n is in the range of 0 to 5. In particular, the reaction has been found compatible with acetals, amides and silyl ethers as functional groups. For fused rings, where the number of substitution sites on the aromatic ring increases, n may be adjusted appropriately. In addition, the above mentioned moieties may be covalently linked to an alcohol moiety in intramolecular reactions.

The alcohol is selected to provide the desired reaction product. In general, the alcohol may be any alcohol such as, but not limited to, alkyl alcohols, including primary, secondary and tertiary alcohols, and phenols. The alcohol may be functionalized. The alcohol may be selected from a wide variety of structural types, including but not limited to, acyclic, cyclic or heterocyclic compounds, fused ring compounds or phenol derivatives. The aromatic compound and the alcohol may be included as moieties of a single molecule, whereby the arylation reaction proceeds as an intramolecular reaction. Alternatively, the corresponding alkoxide salt, e.g., NaOR, LiOR, KOR, etc., may be prepared and used in place of the alcohol in eq. 1. When the corresponding alkoxide is used in the reaction, an additional base may not be required.

In preferred embodiments of the invention, there is no need to use large excesses of either reactant—alcohol or aromatic compound. The reaction proceeds quickly and in high yields to the product aryl ether using substantially stoichiometric amount of reagents. Thus, the alcohol may be present in no greater than a two-fold excess and preferably in no greater than a 20% excess relative to the aromatic compound. Alternatively, the aromatic compound may be present in no greater than a two-fold excess and preferably in no greater than a 20% excess relative to the alcohol.

Suitable transition metal catalysts include soluble complexes of platinum, palladium and nickel. Nickel and palladium are particularly preferred and palladium is most preferred. A zero-valent metal center is presumed to participate in the catalytic carbon-oxygen bond forming sequence. Thus, the metal center is desirably in the zero-valent state or is capable of being reduced to metal(0). Suitable soluble palladium complexes include, but are not limited to, tris (dibenzylideneacetone) dipalladium [Pd$_2$(dba)$_3$], bis (dibenzylideneacetone) palladium [Pd(dba)$_2$] and palladium acetate. Alternatively, particularly for nickel catalysts, the active species for the-oxidative-addition step may be in the metal (+1) oxidative-addition state.

The catalyst may also be a complex comprising a bound supporting ligand, that is, a metal-supporting ligand complex. This catalyst complex may include additional ligands as is necessary to obtain a stable complex. By way of example, PdCl$_2$(BINAP) may be prepared in a separate step and used as the catalyst complex set forth in eq. 1.

The active form of the transition metal catalyst is not well characterized. Therefore, it is contemplated that the "transition metal catalyst" of the present invention, as that term is used herein, shall include any transition metal catalyst and/or catalyst precursor as it is introduced into the reaction vessel and which is, if necessary, converted in situ into the active phase, as well as the active form of the catalyst which participates in the reaction.

In preferred embodiments, the transition metal catalyst complex is present in the range of 0.0001 to 20 mol %, and preferably 0.05 to 5 mol %, and most preferably 1–3 mol %, with respect to the limiting reagent, which may be either the aromatic compound or the alcohol (or alkoxide) or both, depending upon which reagent is in stoichiometric excess. In the instance where the molecular formula of the catalyst complex includes more than one metal, the amount of the catalyst complex used in the reaction may be adjusted accordingly. By way of example, Pd$_2$(dba)$_3$ has two metal centers; and thus the molar amount of Pd$_2$(dba)$_3$ used in the reaction may be halved without sacrifice to catalytic activity.

Additionally, heterogeneous catalysts containing forms of these elements are also suitable catalysts for any of the transition metal catalyzed reactions of the present invention. Catalysts containing palladium and nickel are preferred. It is expected that these catalysts will perform similarly because they are known to undergo similar reactions, namely oxidative-addition reactions and reductive-elimination reactions, which are thought to be involved in the formation of the aryl ethers of the present invention. However, the different ligands are thought to modify the catalyst performance by, for example, modifying reactivity and preventing undesirable side reactions.

The catalyst complex is usually used in combination with supporting ligands. The supporting ligand may be added to the reaction solution as a separate compound or it may be complexed to the metal center to form a metal-supporting ligand complex prior to its introduction into the reaction solution. Supporting ligands are compounds added to the reaction solution which are capable of binding to the catalyst metal center, although an actual metal-supporting ligand complex has not been identified in each and every synthesis. In some preferred embodiments, the supporting ligand is a chelating ligand. Although not bound by any theory of operation, it is hypothesized that the supporting ligands prevent unwanted side reactions as well as enhancing the rate and efficiency of the desired process. Additionally, they often aid in keeping the metal catalyst soluble. Although the present invention does not require the formation of a metal-supporting ligand complex, such complexes have been shown to be consistent with the postulate that they are intermediates in these reactions and it has been observed the selection of the supporting ligand has an affect on the course of the reaction.

The supporting ligand is present in the range of 0.0001 to 40 mol % relative to the limiting reagent, i.e., alcohol or aromatic compound. The ratio of the supporting ligand to catalyst complex is typically in the range of about 1 to 20, and preferably in the range of about 1 to 4 and most preferably about 2.4. These ratios are based upon a single metal complex and a single binding site ligand. In instances where the ligand contains additional binding sites (i.e., a chelating ligand) or the catalyst contains more than one metal, the ratio is adjusted accordingly. By way of example, the supporting ligand BINAP contains two coordinating phosphorus atoms and thus the ratio of BINAP to catalyst is adjusted downward to about 1 to 10, preferably about 1 to 2 and most preferably about 1.2. Conversely, Pd$_2$(dba)$_3$ contains two palladium metal centers and the ratio of ligand to Pd$_2$(dba)$_3$ is adjusted upward to 1 to 40, preferably 1 to 8 and most preferably about 4.8.

Suitable supporting ligands, such as by way of example only, include alkyl and aryl derivatives of phosphines, bisphosphines, imines, amines, arsines, phenols and hybrids thereof, including hybrids of phosphines with amines and or ethers. Suitable phosphine ligands include P(o-tolyl)$_3$. Bis (phosphine) ligands are particularly preferred chelating supporting ligands. Suitable bis(phosphine) compounds include but are in no way limited to (±)-2,2'-bis (diphenylphosphino)-1 ,1'-binaphthyl (and separate enantiomers), (±)-2,2'-bis(di-p-tolylphosphino)- 1,1'-binaphthyl (and separate enantiomers), 1-1'-bis (diphenylphosphino)ferrocene, 1,3-bis(diphenylphosphino) propane; 1 ,2-bis(diphenylphosphino)benzene, and 1 ,2-bis (diphenylphosphino)ethane. Hybrid chelating ligands such as (±)-N,N-dimethyl-1-[2-(diphenylphosphino) ferrocenyl] ethylamine (and separate enantiomers), and (±)-(R)-1-[(S)-2-(diphenylphosphino)-ferrocenyl]ethyl methyl ether (and separate enantiomers) are also within the scope of the invention.

In general, a variety of bases may be used in practice of the present invention. The base is desirably capable of extraction of a proton to promote metal-alkoxide formation. It has not been determined if deprotonation occurs prior to or after oxygen coordination. The base may optionally be sterically hindered to discourage metal coordination of the base in those circumstances where such coordination is possible, i.e., alkali metal alkoxides. By way of example only, suitable bases include NaH, LiH, KH, K$_2$CO$_3$, Na$_2$CO$_3$, Tl$_2$CO$_3$, Cs$_2$CO$_3$, K(OtBu), Li(OtBu), Na(OtBu) K(OPh), Na(OPh), triethylamine or mixtures thereof. NaH, Na(OtBu) and K$_2$CO$_3$ have been found useful in a wide variety of aryl ether bond forming reactions. Base is used in approximately stoichiometric proportions in reaction using alcohol. The present invention has demonstrated that there is no need for large excesses of base in order to obtain good yields of aryl ether under mild reaction conditions. No more than four equivalents and preferably no more than two equivalents are needed. Further, in reactions using the corresponding alkoxide as the reagent, there may be no need for additional base.

The reaction proceeds at mild temperatures to give high yields of the product aryl it ether. Thus, yields of greater than 45%, preferably greater than 75% and even more preferably greater than 80% may be obtained by reaction at mild temperatures according to the invention. The reaction may be carried out at temperature less than 120° C., and preferably in the range of 50–120° C. In one preferred embodiment, the reaction is carried out at a temperature in the range of 80–100° C.

While not being bound by any particular mode of operation, it is hypothesized that the mechanism of the Pd-catalyzed synthesis of aryl ethers most likely proceeds via a pathway roughly similar to that suggested for a palladium-catalyzed arylamination reaction. The Figure presents a proposed reaction pathway for the synthesis of a heterocyclic ether via an intramolecular reaction. Phosphine ligands have been omitted for clarity. With reference to the Figure, oxidative addition of the Pd(0)L$_n$ complex with the aryl halide affords the Pd(II) organometallic complex intermediate A. In the presence of a suitable base, reaction of the alcohol (or alkoxide) moiety could afford metallacycle C, which would then undergo reductive elimination to yield the oxygen heterocycle. The reaction sequence is expected to be the same for intermolecular reactions.

The invention may be understood with reference to the following examples, which are presented for illustrative purposes only and which are non-limiting. Alcohols and aromatic compounds for intermolecular reactions were all commercially available. Substrates used in intramolecular reactions were prepared using standard synthetic organic methods in about 3–5 synthetic steps. Palladium catalysts were all commercially available.

Example 1–11. Examples 1–11 demonstrate the versatility of the aryl ether synthetic route of the invention. A variety of substituted aromatic compounds with attached alcohol moieties were subjected to palladium-catalyzed cross coupling to afford variously substituted heterocyclic ethers. The starting aromatic compounds and alcohols are reported in Table 1. The reactions were carried out as described in the legend.

As shown in Table 1, five, six and seven-membered heterocycles were obtained in good yields from the corresponding aryl halide. In addition, a number of functional groups were found compatible with the reaction conditions including acetals (Example 3), silyl ethers (Example 4), and amides (Example 7). Reactions performed using method A were significantly slower (24–36 h) than reactions performed using method B (1–6 h), however, the reactions using method A were somewhat cleaner. Cyclization of the aryl iodide substrate (Example 2) was extremely slow in toluene, but in 1,4-dioxane, complete conversion occurred in 24–36 h. Two equivalents of ligand relative to palladium (P:Pd=4) and two equivalents of base relative to substrate were used to achieve reasonable yields in the cyclization reactions of Example 11 containing a secondary alcohol. Observed side products included dehalogenation of the aryl halides and in the case of substrates containing secondary alcohols, along with the oxidation of the alcohol to a ketone.

Example 12. This example demonstrates the palladium-catalyzed intermolecular synthesis of the aryl ether, 4-t-butoxybenzonitrile.

A Schlenk tube was charged with Na(OtBu) (97 mg, 1.00 mmol), Pd(OAc)$_2$ (5.6 mg, 0.025 mmol), (R)-(+)-2,2'-bis(di-p-tolylphosphino)-1,1'-binaphthyl(Tol-BINAP) (20.4 mg, 0.030 mmol), 4-bromobenzonitrile (91 mg, 0.50 mmol), and toluene (3 mL).

TABLE 1

Pd-Catalyzed Synthesis of Cyclic Aryl Ethers.

| Entry | Substrate | Method[a] | Product | Yield (%)[b] |
|---|---|---|---|---|
| 1 | [2-bromophenyl-CH$_2$-C(Me)$_2$-OH] | A | [2,2-dimethyl-2,3-dihydrobenzofuran] | 89 |
| 2 | [2-iodophenyl-CH$_2$-C(Me)$_2$-OH] | A | [2,2-dimethyl-2,3-dihydrobenzofuran] | 60 |
| 3 | [2-bromophenyl-CH(OMOM)-CH$_2$-C(Me)$_2$-OH] | A | [MOMO-substituted 2,2-dimethylchroman] | 93 |
| 4 | [2-bromophenyl-CH(OTBDMS)-CH$_2$-C(Me)$_2$-OH] | A | [TBDMSO-substituted 2,2-dimethylchroman] | 90 |
| 5 | [2-bromophenyl-CH$_2$-(1-methyl-2-hydroxycyclopentyl)] | A | [tricyclic Me-substituted cyclopenta-fused chroman] | 65 |

TABLE 1-continued

Pd-Catalyzed Synthesis of Cyclic Aryl Ethers.

| Entry | Substrate | Method[a] | Product | Yield (%)[b] |
|---|---|---|---|---|
| 6 | | A | | 73 |
| 7 | | A | | 66 |
| 8 | | B | | 69 |
| 9 | | B | | 64 |
| 10 | | B | | 73 |
| 11 | | C | | 66 |

[a]Method A: 5 mol % Pd(OAc)$_2$, 6 mol % Tol-BINAP, 1.2 equiv of K$_2$CO$_3$ in toluene at 100° C. Method B: 3 mol % Pd(OAc)$_2$, 3.6 mol % DPPF, 1.2 equiv NaOt-Bu in toluene at 80° C. Method C: 5 mol % Pd(OAc)$_2$, 10 mol % DPPF, 2.0 equiv NaOt-Bu in toluene at 90° C.
[b]Yields refer to average isolated yields of two or more runs.
[c]Reaction was performed in 1,4-dioxane.

The mixture was heated at 100° C. for 30 h under an atmosphere of argon. The mixture was cooled to room temperature and diethyl ether (20 mL) and water (20 mL) were added. The organic layer was separated, washed with brine (20 mL), dried over anhydrous MgSO$_4$, and concentrated in vacuo. The crude product was purified by flash chromatography on silica gel (19/1 hexane/ethyl acetate) to afford 4-t-butoxybenzonitrile as a yellow oil (39 mg, 45% yield).

Example 13. This example demonstrates the palladium-catalyzed intermolecular synthesis of the aryl ether, 4-t-butylphenyl t-butyl ether.

An oven dried Schlenk equipped with a teflon coated stir bar was charged with Na(Ot-Bu) (97 mg, 1.00 mmol), Pd(OAc)$_2$ (5.6 mg, 0.025 mmol), and Tol-BINAP (20.4 mg, 0.030 mmol). The Schlenk was evacuated, back-filled with argon, and charged with toluene (3 mL) and 4-t-butyl bromobenzene (87 µL, 0.50 mmol). The mixture was heated at 100° C. for 40 h at which time the mixture was cooled to room temperature and diethyl ether (20 mL) and water (20 mL) were added. The organic layer was separated, washed with brine (20 mL), dried over anhydrous MgSO$_4$, and concentrated in vacuo. The crude product was purified by flash chromatography on silica gel (99/1 hexane/ethyl acetate) to afford 4-t-butylphenyl t-butyl ether as a yellow oil (59 mg, 53% yield).

Example 14. This example demonstrates the palladium-catalyzed intermolecular synthesis of the aryl ether, 4-benzonitrile cyclopentyl ether.

A Schlenk tube was charged with NaH (80.0 mg, 60% dispersion in mineral oil, 2.00 mmol), cyclopentanol (182 μL, 2.00 mmol), and toluene (2.5 mL). The mixture was heated at 70° C. for 30 minutes under an atmosphere of argon followed by the addition of Pd(OAc)$_2$ (6.7 mg, 0.030 mmol), (R)-(+)-2,2'-bis(di-p-tolylphosphino)-1,1'-binaphthyl (Tol-BINAP) (27.2 mg, 0.040 mmol), 4-bromobenzonitrile (182 mg, 1.00 mmol), and toluene (2.5 mL). The mixture was heated at 100° C. for 1.5 h at which time diethyl ether (30 mL) and water (30 mL) were added at room temperature. The organic layer was separated, washed with brine (20 mL), dried over anhydrous MgSO$_4$, and concentrated in vacuo. The crude product was purified by flash chromatography on silica gel (19/1 hexane/ethyl acetate) to afford 4-benzonitrile cyclopentyl ether as a colorless oil (140 mg, 75% yield).

Example 15. This example demonstrates the palladium-catalyzed intermolecular synthesis of the aryl ether, 4-benzonitrile isopropyl ether.

An oven dried Schlenk tube equipped with a teflon coated stir bar was charged with NaH (60% dispersion in mineral oil, 40 mg, 1.00 mmol), placed under vacuum, and back-filled with argon. To this was added 2-propanol (46 μL, 0.60 mmol) and toluene (2 mL). The mixture was heated at 50° C. for 15 min at which time the 4-bromobenzonitrile (91 mg, 0.50 mmol), Pd$_2$(dba)$_3$ (6.9 mg, 0.0075 mmol), (R)-(+)-2,2'-bis(di-p-tolylphosphino)-1,1'-binaphthyl (Tol-BINAP) (12.2 mg, 0.018 mmol), and 1 mL of toluene were added. The mixture was heated to 50° C. while under an atmosphere of argon. After 22 h, water (50 mL) and diethyl ether (50 mL) were added and the aqueous layer separated and extracted with diethyl ether (50 mL). The organics were combined, washed with brine (50 mL) and dried over anhydrous MgSO$_4$. The crude product was purified by flash chromatography on silica gel (19:1 hexane/ethyl acetate) to afford 4-benzonitrile isopropyl ether (65 mg, 80% yield) as a white solid.

Example 16. This example demonstrates the palladium-catalyzed intermolecular synthesis of the aryl ether, 1-naphthyl cyclohexyl ether.

An oven dried Schlenk tube equipped with a teflon coated stir bar was charged with NaH (40 mg, 1.50 mmol), toluene (2 mL) and cyclohexanol (94 μL, 0.90 mmol). The mixture was heated to 70° C. for 10 min under an atmosphere of argon. To this was added 1-bromonaphthalene (104 μL, 0.75 mmol), Pd$_2$(dba)$_3$ (10.3 mg, 0.0113 mmol), (R)-(+)-2,2'-bis(di-p-tolylphosphino)-1,1'-binaphthyl(Tol-BINAP) (18.3 mg, 0.027 mmol), and 2 mL of toluene. The mixture was heated to 70° C. for 20 h at which time water (60 mL) and diethyl ether (60 mL) were added. The aqueous layer was separated and extracted with diethyl ether (60 mL). The organics were combined, washed with brine (60 mL) and dried over anhydrous MgSO$_4$. The drying agent was removed by filtration and the mother liquor concentrated in vacuo. The crude product was purified by flash chromatography on silica gel (50:1 hexanes:ethyl acetate) to afford 1-naphthyl cyclohexyl ether (101 mg, 60% yield) as a colorless oil.

Example 17. This example demonstrates the palladium-catalyzed intermolecular synthesis of the aryl ether, 3-pentyl-(4-trifluoromethylphenyl) ether.

An oven dried Schlenk tube equipped with a teflon coated stir bar was charged with NaH (60% dispersion in mineral oil, 60 mg, 1.50 mmol), placed under vacuum and back-filled with argon. To this was added toluene (2 mL) and 3-pentanol (98 μL, 0.90 mmol). The mixture was heated at 70° C. for 10 min at which time 4-bromobenzotrifluoride (105 μL, 0.75 mmol), Pd$_2$(dba)$_3$ (10.3 mg, 0.0113 mmol), (R)-(+)-2,2'-bis(di-p-tolylphosphino)-1,1'-binaphthyl (Tol-BINAP) (18.3 mg, 0.027 mmol), and 1 mL of toluene were added. The mixture was heated to 70° C. for 18 h at which time diethyl ether (60 mL) and water (60 mL) were added. The aqueous layer was separated and extracted with diethyl ether (60 mL). The organics were combined, washed with brine (60 mL) and dried over MgSO$_4$. The drying agent was removed by filtration and the mother liquor concentrated in vacuo. The crude product was purified by flash chromatography on silica gel (19:1 hexanes:ethyl acetate) to afford 3-pentyl-(4-trifluoromethylphenyl) ether (114 mg, 54% yield) as a colorless oil.

Example 18. This example demonstrates the palladium-catalyzed intermolecular synthesis of the aryl ether, 9-anthryl cyclopentyl ether.

An oven dried Schlenk tube equipped with a teflon coated stir bar was charged with NaH (60% dispersion in mineral oil, 60 mg, 1.50 mmol), placed under vacuum and back-filled with argon. To this was added toluene (2 mL) and cyclopentanol (109 μL, 0.90 mmol). The mixture was heated at 70° C. for 15 min at which time 9-bromoanthracene (193 μL, 0.75 mmol), Pd$_2$(dba)$_3$ (10.3 mg, 0.0113 mmol), (R)-(+)-2,2'-bis(di-p-tolylphosphino)-1,1'-binaphthyl (Tol-BINAP) (18.3 mg, 0.027 mmol), and 2 mL of toluene were added. The mixture was heated at 100° C. under an atmosphere of argon. After 20 hours diethyl ether (30 mL) and brine (30 mL) were added. The organic layer was separated and dried over anhydrous MgSO$_4$. The drying agent was removed by filtration and the mother liquor concentrated in vacuo. The crude product was purified by flash chromatography on silica gel (99:1 hexanes:ethyl acetate) to afford 9-anthryl cyclopentyl ether (135 mg, 68% yield) as a yellow solid Example 19. This example demonstrates the palladium-catalyzed intermolecular synthesis of the aryl ether, 4-benzonitrile benzyl ether.

An oven dried Schlenk tube equipped with a teflon coated stir bar was charged with NaH (60% dispersion in mineral oil, 60 mg, 1.50 mmol), placed under vacuum and back-filled with argon. To this was added toluene (2 mL) and benzyl alcohol (93 μL, 0.90 mmol). The mixture was heated at 70° C. for 10 min at which time 4-bromobenzonitrile (136 μL, 0.75 mmol), Pd$_2$(dba)$_3$ (10.3 mg, 0.0113 mnmol), (R)-(+)-2,2'-bis(di-p-tolylphosphino)- 1, 1'-binaphthyl (Tol-BINAP) (18.3 mg, 0.027 mmol), and 1 mL of toluene were added. The mixture was heated at 70° C. under an atmosphere of argon. After 14 hours diethyl ether (50 mL) and water (50 mL) were added. The aqueous layer was separated and extracted with diethyl ether (50 mL). The organics were combined, washed with brine (50 mL), and dried over MgSO$_4$. The drying agent was removed by filtration and the mother liquor concentrated in vacuo. The crude product was purified by flash chromatography on silica gel (19:1 hexanes:ethyl acetate) to afford 4-benzonitrile benzyl ether (113 mg, 72% yield) as a white solid.

Example 20. This example demonstrates the palladium-catalyzed intermolecular synthesis of the aryl ether, 4-benzonitrile methyl ether.

An oven dried Schlenk tube equipped with a teflon coated stir bar was charged with NaH (60% dispersion in mineral oil, 60 mg, 1.50 mmol), placed under vacuum and back-filled with argon. To this was added toluene (2 mL) and methyl alcohol (87 μL, 0.90 mmol). Ihe mixture was heated at 70° C. for 10 min at which time 4-bromobenzonitrile (136 μL, 0.75 mmol), Pd$_2$(dba)$_3$ (10.3 mg, 0.0113 mmol), (R)-(+)-2,2'-bis(di-p-tolylphosphino)-1,1'-binaphthyl (Tol- BINAP) (18.3 mg, 0.027 mmol), and 1 mL of toluene were added. The mixture was heated at 70° C. under an atmosphere of argon. After 20 hours diethyl ether (50 mL) and water (50 mL) were added. The aqueous layer was separated and extracted with diethyl ether (50 mL). The organics were combined, washed with brine (50 mL), and dried over MgSO$_4$. The drying agent was removed by filtration and the mother liquor concentrated in vacuo. The crude product was purified by flash chromatography on silica gel (19:1 hexanes:ethyl acetate) to afford 4-benzonitrile methyl ether (77 mg, 77% yield) as a white solid.

Other embodiments of the invention will be apparent to the skilled in the art from a consideration of the specification or practice of the invention disclosed herein. It is intended that the specification and examples be considered as exemplary only with the true scope and spirit of the invention being indicated by the following claims.

What is claimed is:

1. A method of preparing an aryl ether, represented by the following reaction:

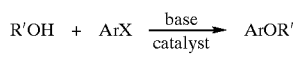

wherein

R' is selected from the group consisting of optionally substituted alkyl, heteroalkyl, aryl, and heteroaryl;

Ar represents an optionally substituted aromatic or heteroaromatic group;

catalyst is a complex comprising a transition metal, selected from the group consisting of platinum, palladium, and nickel, and a supporting ligand;

base is selected from the group consisting of hydrides, carbonates, alkoxides, aryloxides, and amides; and X is selected from the group consisting of halides, sulfonates, diazonium and alkylthio.

2. A method of preparing an aryl ether, represented by the following reaction:

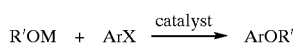

wherein

R' is selected from the group consisting of optionally substituted alkyl, heteroalkyl, aryl, and heteroaryl;

Ar represents an optionally substituted aromatic or heteroaromatic group;

catalyst is a complex comprising a transition metal, selected from the group consisting of platinum, palladium, and nickel, and a supporting ligand;

M represents a cation; and

X is selected from the group consisting of halides, sulfonates, diazonium and alkylthio.

3. The method of claim 1 or 2, wherein X is selected from the group consisting of chloride, bromide, iodide, triflate, mesylate and tosylate.

4. The method of claim 1 or 2, wherein X is bromide.

5. The method of claim 1 or 2, wherein Ar represents an optionally substituted monocyclic aromatic or heteroaromatic group.

6. The method of claim 1 or 2, wherein catalyst is a complex comprising palladium and a supporting ligand.

7. The method of claim 1 or 2, wherein the supporting ligand is a chelating bis(phosphine).

8. The method of claim 1 or 2, wherein R' is an optionally substituted alkyl.

9. The method of claim 1 or 2, wherein the reaction is intramolecular.

10. The method of claim 1 or 2, wherein X is selected from the group consisting of chloride, bromide, iodide, triflate, mesylate and tosylate; and catalyst is a complex comprising palladium and a supporting ligand.

11. The method of claim 10, wherein the supporting ligand is a chelating bis(phosphine).

12. The method of claim 1 or 2, wherein X is bromide; and catalyst is a complex comprising palladium and a supporting ligand.

13. The method of claim 12, wherein the supporting ligand is a chelating bis(phosphine).

14. The method of claim 1, wherein base is selected from the group consisting of sodium hydride, lithium hydride, potassium hydride, sodium carbonate, potassium carbonate, cesium carbonate, thallium carbonate, lithium tert-butoxide, sodium tert-butoxide, potassium tert-butoxide, sodium phenoxide and potassium phenoxide.

15. The method of claim 1, wherein base is selected from the group consisting of sodium hydride, potassium carbonate and sodium tert-butoxide.

16. The method of claim 14 or 15, wherein X is selected from the group consisting of chloride, bromide, iodide, triflate, mesylate and tosylate.

17. The method of claim 14 or 15, wherein X is bromide.

18. The method of claim 14 or 15, wherein catalyst is a complex comprising palladium and a supporting ligand.

19. The method of claim 2, wherein M represents lithium, sodium, potassium, cesium, thallium or ammonium.

20. The method of claim 2, wherein M represents sodium or potassium.

21. The method of claim 19 or 20, wherein X is selected from the group consisting of chloride, bromide, iodide, triflate, mesylate and tosylate.

22. The method of claim 19 or 20, wherein X is bromide.

23. The method of claim 21, wherein catalyst is a complex comprising palladium and a supporting ligand.

24. The method of claim 22, wherein catalyst is a complex comprising palladium and a supporting ligand.

* * * * *